(12) United States Patent
Lalleman

(10) Patent No.: US 8,765,108 B2
(45) Date of Patent: Jul. 1, 2014

(54) DETERGENT COSMETIC COMPOSITION COMPRISING AT LEAST FOUR SURFACTANTS, AT LEAST ONE CATIONIC POLYMER AND AT LEAST ONE ZINC SALT

(75) Inventor: Boris Lalleman, Paris (FR)

(73) Assignee: L'Oreal, Paris (FR)

( * ) Notice: Subject to any disclaimer, the term of this patent is extended or adjusted under 35 U.S.C. 154(b) by 520 days.

(21) Appl. No.: 12/644,618

(22) Filed: Dec. 22, 2009

(65) Prior Publication Data
US 2010/0166693 A1    Jul. 1, 2010

Related U.S. Application Data

(60) Provisional application No. 61/147,832, filed on Jan. 28, 2009.

(30) Foreign Application Priority Data

Dec. 22, 2008 (FR) ................................. 08 58956

(51) Int. Cl.
*A61Q 5/02* (2006.01)
*A61K 8/27* (2006.01)
*A61K 8/46* (2006.01)
*A61K 8/44* (2006.01)

(52) U.S. Cl.
USPC .................... 424/70.6; 424/70.24; 424/70.21; 424/70.31

(58) Field of Classification Search
None
See application file for complete search history.

(56) References Cited

U.S. PATENT DOCUMENTS

| 6,379,397 B2 * | 4/2002 | Vidal et al. ................. 8/409 |
| 2003/0150069 A1 | 8/2003 | Kleen et al. |
| 2005/0144739 A1 * | 7/2005 | Lalleman et al. ............. 8/405 |
| 2006/0182697 A1 * | 8/2006 | Lalleman et al. ............ 424/59 |

FOREIGN PATENT DOCUMENTS

| EP | 1 504 749 | 2/2005 |
| EP | 1 541 120 | 6/2005 |
| EP | 1 674 133 | 6/2006 |
| EP | 1 915 981 | 4/2008 |
| JP | 2003-95897 | 4/2003 |
| WO | WO 96/09030 A1 | 3/1996 |
| WO | WO 99/13844 | 3/1999 |

OTHER PUBLICATIONS

Euoprean Search Report for EP 09 30 6254, dated Apr. 28, 2010.
English language Abstract of JP 2003-95897, Apr. 3, 2003.
French Search Report for FR 08/58956, dated Aug. 10, 2009.
English language Abstract of EP 1 541 120, dated Jun. 15, 2005.
English language Abstract of EP 1 915 981, dated Apr. 30, 2008.

* cited by examiner

*Primary Examiner* — H. Sarah Park
(74) *Attorney, Agent, or Firm* — The Marbury Law Group, PLLC

(57) ABSTRACT

The present disclosure relates to a cosmetic composition for keratin fibers, for example, human keratin fibers such as hair, comprising: at least one anionic surfactant (A) comprising, in its structure, at least one group chosen from sulphate, sulphonate, and phosphate groups; at least one carboxylic anionic surfactant (B) other than the at least one anionic surfactant (A); at least one surfactant (C) chosen from amphoteric and zwitterionic surfactants; at least one alkyl(poly)glycoside non-ionic surfactant (D); at least one cationic polymer (E); at least one zinc salt (F); and optionally at least one UV-screening agent (G); and further wherein the weight ratio of the total amount of the surfactants (A), (B), (C), and (D) to the amount of zinc element of the at least one zinc salt has a value of less than 30. The present disclosure also relates to the uses of the disclosed cosmetic compositions for washing keratin fibers, for instance, colored hair, and for protecting the color of the keratin fibers from sunlight and/or repeated washing.

18 Claims, No Drawings

DETERGENT COSMETIC COMPOSITION COMPRISING AT LEAST FOUR SURFACTANTS, AT LEAST ONE CATIONIC POLYMER AND AT LEAST ONE ZINC SALT

This application claims benefit of U.S. Provisional Application No. 61/147,832, filed Jan. 28, 2009. This application also claims benefit of priority under 35 U.S.C. §119 to French Patent Application No. 0858956, filed Dec. 22, 2008.

The present disclosure relates to detergent cosmetic compositions for washing and/or cleansing keratin fibers, for example, human keratin fibers such as the hair, and for instance, colored hair, comprising at least one cationic polymer and at least one zinc salt. The present disclosure also relates to the various uses thereof, for example, for protecting the artificial color of keratin fibers from sunlight and/or repeated washing.

It is known to dye the hair with dyeing compositions comprising oxidation dye precursors, generally known as oxidation bases. These oxidation bases are colorless or weakly colored compounds which, when combined with oxidizing products, give rise to colored compounds via a process of oxidative condensation. The shades obtained with these oxidation bases can be varied by combining them with couplers or color modifiers. The variety of molecules used as regards the oxidation bases and couplers allows a wide range of colors to be obtained.

It is also known practice to dye the hair with a direct dye. The process conventionally used in direct dyeing comprises applying to the hair direct dyes, which are colored and coloring molecules that have affinity for the hair, and leaving them to stand and then rinsing the fibers.

The colorations that result therefrom are chromatic but may be temporary or semi-permanent because of the weak interactions between direct dyes and keratin fiber. In addition, direct dyes may desorb from the surface and/or the core of the fiber, which may be responsible for weak dyeing power and/or poor fastness with respect to washing.

The artificial color of the hair afforded by a direct dyeing or oxidation dyeing treatment may gradually deteriorate after repeated washing and exposure to light, which leads to the fading of the coloration of the hair over time.

The use of rinse-out products and care products does not sufficiently improve the fastness of the artificial color of the hair.

There is therefore a need to find detergent cosmetic compositions that make it possible to improve the fastness of the artificial color of keratin fibers, for instance, human keratin fibers such as the hair and colored hair, with respect to repeated washing and light, while having satisfactory usage qualities.

The inventors have discovered that by using at least one zinc salt, for example, an amount of zinc element in cosmetic compositions, such as detergent cosmetic compositions, it is possible to overcome at least one of the drawbacks mentioned above, for example, to protect, in a more effective and durable manner, the color of said keratin fibers against the degradations caused by light, ultraviolet radiation and/or repeated washing (fading of the color, modification of the initial shade), compared to the known rinse-out products or care products applied in the same quantities, while obtaining at least one of good usage qualities, rinseability, and feel quality after rinsing.

One aspect of the present disclosure is to provide a detergent cosmetic composition for keratin fibers, for example, human keratin fibers such as the hair, or such as colored hair, comprising, in a cosmetically acceptable medium, at least four different surfactants, at least one cationic polymer, at least one organic or inorganic zinc salt, and optionally at least one UV-screening agent in a particular weight ratio of the amount of the surfactants to the amount of zinc element part of the at least one organic or inorganic zinc salt.

Another aspect of the present disclosure relates to the use of a composition according to the present disclosure or for the process of preparing a detergent cosmetic composition for keratin fibers, for example, human keratin fibers such as the hair, including colored hair; for example, the process of preparing a shampoo or a shampoo for colored hair.

Another aspect of the present disclosure relates to the use of a composition according to the present disclosure for washing and/or cleansing keratin fibers, for example, human keratin fibers such as the hair, for instance, colored hair.

Another aspect of the present disclosure is the use of a composition according to the present disclosure for protecting the color of keratin fibers, for example, human keratin fibers such as the hair and colored hair, from sunlight and/or repeated washing.

Other features, aspects, subjects and benefits of the present disclosure will appear yet more clearly on reading the description and examples that follow.

As used herein, "anionic" refers to any compound possessing at least one permanent negative charge, or any compound that can be ionized to a negatively charged entity, and that does not comprise a cationic charge, under the conditions of the use of the compositions of the present disclosure (for example, a medium pH).

As used herein, "cationic" refers to any compound possessing at least one permanent positive charge, or any compound that can be ionized to a positively charged entity and that does not comprise an anionic charge, under the conditions of the use of the compositions of the present disclosure (for example, a medium pH). This definition also applies to a cationic unit.

As used herein, "non-ionic" refers to any compound that is neither cationic nor anionic within the meaning of the present disclosure; for instance, any compound that does not comprise any cationic or anionic group within the meaning of the present application.

The term "cosmetically acceptable" or "physiologically acceptable" is understood to mean that it is compatible with application to the body of a living being, such as the human body, for instance, the scalp and the hair.

For simplification, the following terms can be used:

"surfactant (A)" or "compound (A)" refers to an anionic surfactant having, in its structure, at least one group chosen from sulphate, sulphonate, and phosphate groups, used according to the present disclosure and as described herein;

"surfactant (B)" or "compound (B)" refers to a carboxylic anionic surfactant other than the surfactant (A), used according to the present disclosure and as described herein;

"surfactant (C)" or "compound (C)" refers to at least one surfactant chosen from amphoteric and zwitterionic surfactants used according to the present disclosure and as describedherein;

"surfactant (D)" or "compound (D)" refers to an alkyl (poly)glycoside non-ionic surfactant used according to the present disclosure and as described herein;

"polymer (E)" or "compound (E)" refers to a cationic polymer used according to the present disclosure and as described herein;

"compound (F)" refers to a zinc salt used according to the present disclosure and as described herein;

"screening agent (G)" or "compound (G)" refers to an ultraviolet-screening agent (or referred to as UV-screening agent) used according to the present disclosure and as described herein.

The term "human keratin fibers" is understood to mean the hair, the body hair or bristles, for example, a beard or moustache, the eyelashes, and the eyebrows.

The term "colored keratin fibers" is understood to mean keratin fibers that are artificially dyed, for instance, by a direct dyeing process or by an oxidation dyeing process, in the presence or absence of an oxidizing agent.

The term "oxidizing agent" is understood, within the meaning of the present disclosure, to mean any compound having oxidizing properties and being other than the oxygen from the air.

The term "washing(s)" is understood to mean at least one application of an aqueous composition, such as a detergent aqueous composition or a shampoo, to the keratin fibers, and the removal of the at least one aqueous composition applied to the keratin fibers. This expression also includes bathing, such as in the sea or in a swimming pool.

The compounds (A), (B), (C), (D), (E), (F), and (G) as defined in the various embodiments of the present disclosure are each different from one another.

Unless otherwise indicated, each of the compounds, optional or otherwise, used or envisaged within the context of the present disclosure, may be present alone or in a mixture.

On aspect of the present disclosure relates to a detergent cosmetic composition intended for washing and/or cleansing keratin fibers, for instance, human keratin fibers, such as the hair, or such as the colored hair, comprising:
- at least one anionic surfactant (A) comprising at least one group chosen from sulphate, sulphonate, and phosphate groups,
- at least one carboxylic anionic surfactant (B) other than the at least one anionic surfactant (A),
- at least one surfactant (C) chosen from amphoteric and zwitterionic surfactants,
- at least one alkyl(poly)glycoside non-ionic surfactant (D),
- at least one cationic polymer (E),
- at least one zinc salt (F), and
- optionally at least one UV-screening agent (G), and wherein the weight ratio of the total amount of the surfactants (A), (B), (C), and (D) to the amount of zinc element of the at least one zinc salt has a value of less than 30.

Anionic surfactant (A).

In some embodiments, the at least one surfactant (A) does not comprise, in their structure, carboxylic (COON) groups or carboxylic groups in the salt form (COO−).

In some embodiments, the at least one surfactant (A) is chosen from anionic surfactants comprising, in their structure, at least one group chosen from sulphates and sulphonates.

The at least one surfactant (A) may be oxyethylenated and/or oxypropylenated. The total average number of ethylene oxide (EO) and/or propylene oxide (PO) groups may then vary from 2 to 50 such as from 2 to 10.

In some embodiments, the at least one surfactant (A) may be chosen from alkyl sulphates, alkylamido sulphates, alkyl ether sulphates, alkylamido ether sulphates, alkylaryl ether sulphates, alkyl ether sulphosuccinates, acyl isethionates, methyl acyl taurates, and salts thereof; the alkyl or acyl group of all these various compounds may comprise from 8 to 24 carbon atoms, and the aryl group may be chosen from phenyl and benzyl group.

In some embodiments, the at least one surfactant (A) is in the form of salts, for example, alkali metal salts such as sodium salts, ammonium salts, amine salts such as amino alcohol salts, and/or magnesium salts.

In some embodiments, the at least one anionic surfactant (A) comprising, in its structure, at least one sulphate group and/or at least one sulphonate group may be chosen from $C_8$-$C_{14}$, such as $C_{12}$-$C_{14}$, alkyl sulphates and alkyl ether sulphates. These salts may comprise, for instance, from 2 to 5 ethylene oxide groups. As non-limiting examples, the at least one anionic surfactants (A) may be chosen from sodium, triethanolamine, magnesium, or ammonium ($C_{12}$-$C_{14}$)alkyl sulphates, and sodium, ammonium, or magnesium ($C_{12}$-$C_{14}$) alkyl ether sulphates oxyethylenated, for example, with 2.2 mol of ethylene oxide. Further as non-limiting examples, the at least one surfactant (A) is chosen from sodium, ammonium, or magnesium ($C_{12}$-$C_{14}$)alkyl ether sulphates oxyethylenated with 2.2 mol of ethylene oxide, as sold under the name TEXAPON N702 by Cognis.

The at least one surfactant (A) is present in an amount, for example, ranging from 1% to 50% by weight, such as 2% to 25% by weight, or for instance, 3% to 20% by weight such as 3.5% to 8% by weight, relative to the total weight of the composition.

Carboxylic Anionic Surfactant (B)

According to the present disclosure, the at least one carboxylic anionic surfactant (B) is an anionic surfactant comprising, in its structure, at least one carboxylic functional group (—COOH) optionally in carboxylic acid salt form (—COO−).

The at least one carboxylic anionic surfactant (B) according to the present disclosure is different from the at least one surfactants (A) and for example, does not comprise any sulphate, sulphonate, and/or phosphate groups.

In some embodiments, the at least one surfactant (B) may be chosen from:
- ($C_6$-$C_{24}$)alkyl D-galactoside uronic acids, and salts thereof;
- ($C_6$-$C_{24}$)acyl sarcosinic acids, and salts thereof;
- ($C_6$-$C_{24}$)acyl lactylic acids, and salts thereof; and
- ($C_6$-$C_{24}$)acyl glutamic acids, and salts thereof.

In some embodiments, alkyl(poly)glycoside carboxylic acids, such as the ones in salt form, or as non-limiting examples, alkylglucoside acetates, alkylglucoside citrates, and alkylpolyglycoside tartrates; the alkyl group of these alkyl(poly)glycoside carboxylic acids may comprise from 6 to 24 carbon atoms. Such products are sold, for instance, under the names EUCAROL APG/EC and EUCAROL APG/ET by Lambert' and PLANTAPON LGC Sorb by Cognis.

In some embodiments, the at least one surfactant (B) may be oxyalkylenated, for instance, oxyethylenated and/or oxypropylenated. The total average number of alkylene oxide groups may range from 2 to 50, for example, from 2 to 24 or from 2 to 15.

When the at least one surfactant (B) is oxyalkylenated, they may be chosen from:
- polyoxyalkylenated ($C_6$-$C_{24}$)alkyl ether carboxylic acids;
- polyoxyalkylenated ($C_6$-$C_{24}$)alkylaryl ether carboxylic acids;
- polyoxyalkylenated ($C_6$-$C_{24}$)alkylamido ether carboxylic acids;
- and salts thereof, as non-limiting examples, those comprising from 2 to 50 alkylene oxide groups, such as from 2 to 50 ethylene oxide (EO) groups, or such as from 2 to 15 ethylene oxide groups.

The salts are chosen from, as non-limiting examples, alkali metal salts such as sodium or magnesium salts, ammonium salts, amine salts such as amino alcohol salts or for example, triethanolamine or monoethanolamine salts.

In some embodiments, the at least one surfactant (B) is chosen from:
- $(C_6-C_{24})$acyl glutamic acids, and salts thereof;
- $(C_6-C_{24})$alkylpolyglycoside carboxylic acids, and salts thereof;
- polyoxyalkylenated $(C_6-C_{24})$alkyl ether carboxylic acids and salts thereof, for instance, those comprising from 2 to 24 alkylene oxide groups, such as from 2 to 24 ethylene oxide groups, or such as from 2 to 15 ethylene oxide groups;
- polyoxyalkylenated $(C_6-C_{24})$alkylaryl ether carboxylic acids, and salts thereof, for example, those comprising from 2 to 24 alkylene oxide groups, such as from 2 to 24 ethylene oxide groups, or such as from 2 to 15 ethylene oxide groups;
- polyoxyalkylenated $(C_6-C_{24})$alkylamido ether carboxylic acids and salts thereof, for example, those comprising from 2 to 24 alkylene oxide groups, such as from 2 to 24 ethylene oxide groups, or such as from 2 to 15 ethylene oxide groups.

In some embodiments, the at least one surfactant (B) is chosen from the polyethoxylated carboxylic anionic surfactants that of formula (I):

wherein:

$R_1$ is chosen from linear or branched $C_8-C_{22}$ alkyl and alkenyl groups, $(C_8-C_9)$alkylphenyl groups, and $R_2CONH—CH_2—CH_2—$ groups, wherein $R_2$ is chosen from linear or branched $C_{11}-C_{21}$ alkyl and alkenyl groups;

n is an integer or decimal number (average value) that may range from 2 to 24 such as from 2 to 10;

A is chosen from H, $NH_4$, Na, K, Li, Mg, monoethanolamine, and triethanolamine residues. Mixtures of compounds of formula (I) may also be used, for example, a mixture of compounds of formula (I) wherein the groups $R_1$ are different.

As non-limiting examples, $R_1$ can be chosen from $(C_{12}-C_{14})$alkyl, cocoyl, oleyl, nonylphenyl, and octylphenyl groups; A is chosen from a hydrogen and a sodium atom, and n ranges from 2 to 20 such as ranges from 2 to 10.

Further as non-limiting examples, compounds of formula (I) may be used, wherein $R_1$ is chosen from a $C_{12}$ alkyl group; A is chosen from a hydrogen and a sodium atom, and n ranges from 2 to 10.

Among the commercial products, non-limiting examples include products sold by the company Chem Y under the names:
- AKYPO® NP 70 ($R_1$=nonylphenyl, n=7, A=H)
- AKYPO® NP 40 ($R_1$=nonylphenyl, n=4, A=H)
- AKYPO® OP 40 ($R_1$=octylphenyl, n=4, A=H)
- AKYPO® OP 80 ($R_1$=octylphenyl, n=8, A=H)
- AKYPO® OP 190 ($R_1$=octylphenyl, n=19, A=H)
- AKYPO® RLM 38 ($R_1$=$C_{12}$-$C_{14}$ alkyl, n=4, A=H)
- AKYPO® RLM 38 NV ($R_1$=$C_{12}$-$C_{14}$ alkyl, n=4, A=Na)
- AKYPO® RLM 45 CA ($R_1$=$C_{12}$-$C_{14}$ alkyl, n=4.5, A=H)
- AKYPOO® RLM 45 NV ($R_1$=$C_{12}$-$C_{14}$ alkyl, A=Na)
- AKYPO® RLM 100 ($R_1$=$C_{12}$-$C_{14}$alkyl, n=10, A=H)
- AKYPO® RLM 100 NV ($R_1$=$C_1$-$C_{14}$alkyl, n=10, A=Na)
- AKYPO® RLM 130 ($R_1$=$C_{12}$-$C_{14}$ alkyl, n=13, A=H)
- AKYPO® RLM 160 NV ($R_1$=$C_{12}$-$C_{14}$alkyl, n=16, A=Na), or by SANDOZ under the names:
- SANDOPAN DTC-Acid ($R_1$=$C_{1-3}$ alkyl, n=6, A=H)
- SANDOPAN DTC ($R_1$=$C_{13}$ alkyl, n=6, A=Na)
- SANDOPAN LS 24 ($R_1$=$C_{12}$-$C_{14}$ alkyl, n=12, A=Na)
- SANDOPAN JA 36 ($R_1$=$C_{13}$ alkyl, n=18, A=H), for example, the products sold under the following names:
- AKYPO® RLM 45 (INCI: Laureth-5 carboxylic acid)
- AKYPO® RLM 100
- AKYPO® RLM 38.

The at least one surfactant (B) is present in an amount, for example, ranging from 0.5% to 15% by weight, such as from 1% to 10% by weight, or such as from 1.5% to 8% by weight, relative to the total weight of the composition.

Amphoteric and/or Zwitterionic Surfactant (C)

In some embodiments, the at least one surfactant (C) chosen from amphoteric and zwitterionic surfactants may be chosen from aliphatic secondary amine derivatives and aliphatic tertiary amine derivatives, wherein the at least one aliphatic substituent of the secondary or tertiary amine functional group is chosen from linear or branched chains comprising 8 to 22 carbon atoms and comprising at least one group chosen from water-soluble anionic groups (such as, for example, a carboxylate, sulphonate, sulphate, phosphate, and/or phosphonate group) and betaines (such as those mentioned below).

Among the amine derivatives that can be used within the context of the present disclosure, non-limiting mention may be made, alone or as mixtures, of the products described in U.S. Pat. No. 2,528,378 and U.S. Pat. No. 2,781,354 and those chosen from the structures of formula (II) or (III) below:

formula (II):

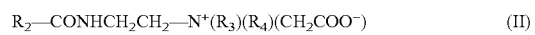

wherein:

$R_2$—CO is chosen from $C_6-C_{24}$ acyl groups, for example, the $C_6-C_{24}$ acyl part corresponding to one of the fatty acids of formula $R_2$—COOH present in hydrolyzed coconut oil, an octoyl group, a decoyl group, or a dodecanoyl group, or a mixture of these groups;

$R_3$ is chosen from a β-hydroxyethyl group; and $R_4$ is chosen from a carboxymethyl group.

formula (III):

wherein:

B is chosen from —$CH_2CH_2OX'$;

C is chosen from —$(CH_2)_z$—Y', with z=1 or 2;

X' is chosen from the —$CH_2CH_2$—COOH group or a hydrogen atom;

Y' is chosen from —COOH or the —$CH_2$—CHOH—$SO_3H$ group;

$R_2$—CO is chosen from a $C_6-C_{24}$ acyl group, for example, the $C_6-C_{24}$ acyl part corresponding to one of the fatty acids of formula $R_2$—COOH present in hydrolyzed coconut oil or linseed oil, an octoyl group, a decoyl group, a dodecanoyl group, a stearoyl group, an isostearoyl group, or an oleoyl group, or a mixture of these groups.

These compounds may be classified in the CTFA dictionary under the names disodium cocoamphodiacetate, disodium lauroamphodiacetate, disodium caprylamphodiacetate, disodium caprylloamphodiacetate, disodium cocoamphodipropionate, disodium lauroamphodipropionate, disodium caprylamphodipropionate, disodium caprylloamphodipropionate, lauroamphodipropionic acid, and cocoamphodipropionic acid.

By way of example, non-limiting mention may be made of disodium cocoamphodiacetate, sold under the trade name MIRANOL® C2M CONCENTRATE by the company Rhodia Chimie.

Among the betaines that can be used within the context of the present disclosure, non-limiting mention may be made of $(C_8-C_{20})$alkylbetaines, sulphobetaines, $(C_8-C_{20})$alkylamido $(C_1-C_6)$alkylbetaines, and $(C_8-C_{20})$alkylamido$(C_1-C_6)$alkylsulphobetaines; the betaines may be optionally hydroxylated, and may be used alone or as mixtures.

In some embodiments, the at least one amphoteric and/or zwitterionic surfactant (C) is chosen from the above betaines and mixtures thereof. For example, ($C_8$-$C_{20}$)alkylbetaines may be used, such as the cocobetaine sold by Cognis under the name DEHYTON AB 30 as an aqueous solution comprising 30% by weight of active material (AM) relative to the total weight of the solution; ($C_8$-$C_{20}$)alkylamido($C_1$-$C_6$)alkylbetaines, for instance, cocamidopropylbetaine as sold under the name TEGOBETAINE® F50 by Goldschmidt.

Further as non-limiting example, the at least one amphoteric and/or zwitterionic surfactant (C) is chosen from betaines.

The at least one amphoteric and/or zwitterionic surfactant (C) may be present in an amount ranging from, for instance, 0.1% to 20% by weight, such as from 1% to 15% by weight, or such as from 2% to 10% by weight, relative to the total weight of the composition.

Alkyl(poly)glycoside Non-ionic Surfactant (D)

As used herein, the term "alky(poly)glycoside" is understood to denote an alkylpolyglycoside or an alkylmonoglycoside, also referred to as alkylglycoside in the present disclosure, which may be alkoxylated by at least one alkylene oxide group, such as $C_2$-$C_4$ alkylene oxide groups.

In some embodiments, the at least one alkyl(poly)glycoside non-ionic surfactant (D) may be chosen from surfactants of formula (IV) below:

$$R_1O-(R_2O)_t(G)_v \qquad (IV)$$

wherein:

$R_1$ is chosen from linear or branched, saturated or unsaturated alkyl groups comprising from 8 to 24 carbon atoms, and alkylphenyl groups comprising linear or branched alkyl group comprises from 8 to 24 carbon atoms;

$R_2$ is chosen from alkylene groups comprising from about 2 to 4 carbon atoms;

G is chosen from sugar units comprising from 5 to 6 carbon atoms;

t is chosen from a value ranging from 0 to 10, such as from 0 to 4; and v is chosen from a value ranging from 1 to 15.

As non-limiting examples, the at least one alkyl(poly)glycoside non-ionic surfactant (D) corresponds to the formula (IV), wherein:

$R_1$ is chosen from linear or branched, saturated or unsaturated alkyl group comprising from 8 to 18 carbon atoms;

G is chosen from glucose, fructose, and galactose, such as chosen from glucose;

t is chosen from a value ranging from 0 to 3, such as t equal to 0; and $R_2$ and v are as defined previously.

The degree of polymerization of the at least one alkyl(poly)glycoside non-ionic surfactant (D), as represented, for example, by the index v in the formula (IV), ranges on average from 1 to 15, such as from 1 to 4. Further as an example, this degree of polymerization may range from 1 to 2, such as from 1.1 to 1.5, on average.

The glycoside bonds between the sugar units may be of 1, 6 or 1,4 type such as 1,4 type.

As non-limiting examples, the compounds of formula (IV) that may be used in the present disclosure may be chosen from the products sold by Cognis under the names PLANTAREN® (600 CS/U, 1200 and 2000) or PLANTACARE® (818, 1200 and 2000). It is also possible to use the products sold by SEPPIC under the names TRITON CG 110 (or ORAMIX CG 110) and TRITON CG 312 (or ORAMIX® NS 10), the products sold by BASF under the name LUTENSOL GD 70 or the products sold by ChemY under the name AG10 LK.

It is also possible to use the ($C_8$-$C_{16}$)alkylpolyglucoside-1,4, for example, as an aqueous solution at a concentration of 53% by weight of the total weight of the solution, sold by Cognis under the reference PLANTACARE® 818 UP.

The at least one alkyl(poly)glycoside non-ionic surfactant (D) may be present in an amount ranging from, for instance, 0.1% to 20% by weight, such as from 1% to 15% by weight, relative to the total weight of the composition.

In some embodiments, the minimum amount of anionic, amphoteric and/or zwitterionic, and non-ionic surfactants is the amount that is sufficient to give the composition satisfactory latherability and/or detergent power.

Thus, according to the present disclosure, the total amount of anionic, amphoteric and/or zwitterionic, and non-ionic surfactants may range from 4% to 50% by weight, such as from 6% to 35% by weight, or such as from 8% to 25% by weight, of the total weight of the composition.

The weight ratio of the amount of the at least one surfactant (A) to the amount of the at least one surfactant (B) may have a value ranging from 0.1 to 10, for example, from 0.5 to 5.

The weight ratio of the amount of the at least one surfactant (A) to the amount of the at least one surfactant (C) may have a value ranging from 0.1 to 10, for example, from 0.5 to 5, such as from 0.7 to 2.

The weight ratio of the amount of the at least one surfactant (A) to the amount of the at least one surfactant (D) may have a value ranging from 0.1 to 10, for example, from 0.2 to 5, such as from 0.5 to 2.

The weight ratio of the amount of the at least one anionic surfactant (B) to the amount of the at least one surfactant (C) may have a value ranging from 0.1 to 10, for example, from 0.2 to 5, such as from 0.2 to 5.

Cationic Polymer (E)

In some embodiments, the at least one cationic polymer (E) that can be used in accordance with the present disclosure may be chosen from those known for improving the cosmetic properties of hair treated with detergent compositions, for example, those described in European Patent Application No. EP-A-0 337 354 and in French Patent Application Nos. FR-A-2 270 846, FR-A-2 383 660, FR-A-2 598 611, FR-A-2 470 596, FR-A-2 519 863, and FR-A-2 875 503.

In some embodiments, the at least one cationic polymer (E) is chosen from those that comprise, in their structure, units comprising primary, secondary, tertiary, and/or quaternary amine groups that may, for example, either be part of the main polymer chain, or be borne by a side substituent directly connected to this main polymer chain.

In some embodiments, the at least one cationic polymer (E) is, chosen from polymers of the family of polyamines, polyamino amides, and polyquaternary ammoniums. Among these polymers, non-limiting mention may be made of:

(1) homopolymers or copolymers derived from crosslinked or uncrosslinked, acrylic or methacrylic esters or amides comprising at least one unit chosen from the units of the formulae (V), (VI), (VII), and (VIII) below:

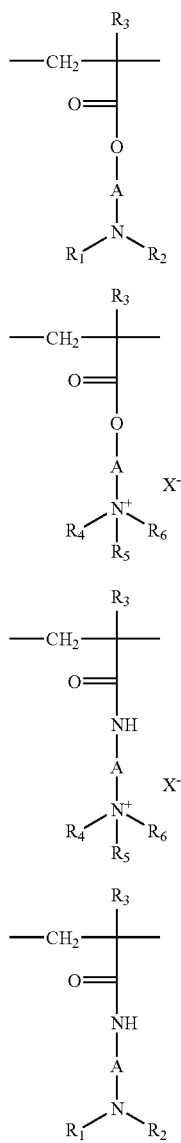

wherein:

$R_1$ and $R_2$, which may be identical or different, are chosen from a hydrogen atom and alkyl groups having from 1 to 6 carbon atoms, such as chosen from methyl and ethyl;

$R_3$, which may be identical or different, is chosen from a hydrogen atom and a $CH_3$ group;

A, which may be identical or different, is chosen from linear or branched alkyl groups comprising 1 to 6 carbon atoms such as 2 or 3 carbon atoms, and hydroxyalkyl groups comprising 1 to 4 carbon atoms;

$R_4$, $R_5$, $R_6$, which may be identical or different, are chosen from alkyl groups having from 1 to 6 carbon atoms and a benzyl group; for example, are chosen from alkyl groups having from 1 to 6 carbon atoms;

$X^-$ is chosen from anions derived from an inorganic or organic acid, such as a methosulphate anion or a halide such as chloride or bromide.

The polymers of family (1) can also contain at least one unit deriving from comonomers that may be chosen from the family of acrylamides, methacrylamides, diacetone acrylamides, acrylamides, and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), non-limiting mention may be made of:

the copolymers of acrylamide and of dimethylaminoethyl methacrylate quaternized with dimethyl sulphate or with a dimethyl halide, such as the one sold under the name HERCOFLOC by Hercules;

the copolymers of acrylamide and of methacryloyloxyethyltrimethylammonium chloride described, for example, in European Patent Application No. EP A 080 976 and sold under the name BINA QUAT P 100 by Ciba Geigy;

the copolymer of acrylamide and of methacryloyloxyethyltrimethylammonium methosulphate, sold under the name RETEN by Hercules;

quaternized or non-quaternized vinylpyrrolidone/dialkylaminoalkyl acrylate or methacrylate copolymers, for instance the products sold under the name GAFQUAT by ISP such as, for example, GAFQUAT 734 or GAFQUAT 755 or else the products named COPOLYMER 845, 958 and 937. These polymers are described in detail in French Patent Nos. FR 2 077 143 and FR 2 393 573;

the dimethylaminoethyl methacrylate/vinylcaprolactam/vinylpyrrolidone terpolymers such as the product sold under the name GAFFIX VC 713 by ISP;

the vinylpyrrolidone/methacrylamidopropyldimethylamine copolymer sold, for instance, under the name STYLEZE CC 10 by ISP;

the quaternized vinylpyrrolidone/dimethylaminopropylmethacrylamide copolymers such as the product sold under the name GAFQUAT HS 100 by ISP;

the crosslinked polymers of methacryloyloxy($C_1$-$C_4$)alkyl tri($C_1$-$C_4$)alkylammonium salts such as the polymers obtained by homopolymerization of dimethylaminoethyl methacrylate quaternized by methyl chloride, or by copolymerization of the acrylamide with the dimethylaminoethyl methacrylate quaternized by methyl chloride, the homopolymerization or copolymerization being followed by crosslinking with an olefinically unsaturated compound, such as methylenebisacrylamide. As a non-limiting example, a crosslinked acrylamide/methacryloyloxyethyltrimethylammonium chloride (20/80 by weight) copolymer in the form of a dispersion comprising 50% by weight of said copolymer in inorganic oil. This dispersion is sold under the name SALCARE® SC 92 by Ciba. Further as a non-limiting example, a crosslinked homopolymer of methacryloyloxyethyl-trimethylammonium chloride comprising around 50% by weight of the homopolymer in inorganic oil or in a liquid ester. These dispersions are sold under the names SALCARE® SC 95 and SALCARE® SC 96 by Ciba.

(2) Cationic polysaccharides, for example, chosen from:

a) Cellulose ether derivatives comprising quaternary ammonium groups described in French Patent No. FR 1 492 597, and for instance, the polymers sold under the names "JR" (JR 400, JR 125, JR 30M) or "LR" (LR 400, LR 30M) by Union Carbide Corporation. These polymers are also defined in the CTFA dictionary as quaternary ammoniums of hydroxyethyl cellulose that have reacted with an epoxide substituted by a trimethylammonium group.

b) Cellulose copolymers or cellulose derivatives grafted with a water-soluble quaternary ammonium monomer, described for example, in U.S. Pat. No. 4,131,576, such as hydroxyalkyl celluloses, for instance hydroxymethyl, hydroxyethyl, or hydroxypropyl celluloses grafted, for example, with a methacryloylethyltrimethylammonium, methacrylamidopropyltrimethylammonium, or dimethyldiallylammonium salt.

The products sold corresponding to this definition include but not limited to, the products sold under the names Celquat L 200 and Celquat H 100 by National Starch.

c) Guar gums comprising cationic trialkylammonium groups. Use is made, for example, of guar gums modified by a salt (for example, a chloride salt) of 2,3-epoxypropyltrimethylammonium.

Such products may be sold, for example, under the trade names JAGUAR C13 S, JAGUAR C 15, JAGUAR C 17 or JAGUAR C162 by Meyhall.

(3) Polymers comprising piperazinyl units and divalent alkylene or hydroxyalkylene radicals comprising linear or branched chains, optionally interrupted by oxygen, sulphur, or nitrogen atoms, or by aromatic or heterocyclic rings, and also the oxidation and/or quaternization products of these polymers. Non-limiting examples of such polymers include the ones described in French Patent Nos. FR 2 162 025 and FR 2 280 361.

(4) Water-soluble cationic polyamino amides prepared, for example, by polycondensation of an acid compound with a polyamine; these polyamino amides can be crosslinked with at least one compound chosen from epihalohydrin, diepoxide, dianhydride, unsaturated dianhydride, bis-unsaturated derivative, bis-halohydrin, bis azetidinium, bis-haloacyldiamine, bis-alkyl halide, and oligomers resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; these polyamino amides can be alkylated or, if they contain at least one tertiary amine functional group, they can be quaternized; for example, when the cationic polyaminoamides comprises at least one tertiary amine functional group and/or at least one quaternized amine functional group, the cationic polyaminoamides is optionally alkylated. Such polymers may be the ones described in, for example, French Patent Nos. FR 2 252 840 and FR 2 368 508.

(5) Polyamino amide derivatives resulting from the condensation of polyalkylene polyamines with polycarboxylic acids followed by alkylation with difunctional agents. Non-limiting mention may be made, for example, of adipic acid/dialkylaminohydroxylalkyl-dialkylenetriamine polymers in which the alkyl group comprises from 1 to 4 carbon atoms such as the ones chosen from methyl, ethyl, and propyl. Such polymers may be the ones described in, for example, French Patent No. FR 1 583 363.

Among these derivatives, non-limiting mention may be made of the adipic acid/dimethylaminohydroxypropyl/diethylenetriamine polymers sold under the name CARTARETINE F, F4 or F8 by Sandoz.

(6) Polymers obtained by the reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranging from 0.8:1 to 1.4:1; the polyamino amide resulting therefrom being made to react with epichlorohydrin in a molar ratio of epichlorohydrin relative to the secondary amine group of the polyamino amide ranging from 0.5:1 to 1.8:1. Such polymers may be the ones described in U.S. Pat. Nos. 3,227,615 and 2,961,347.

Additional non-limiting examples of polymers of this type include the ones sold under the name HERCOSETT 57 by Hercules Inc. or else under the name PD 170 or DELSETTE 101 by Hercules in the case of the adipic acid/epoxypropyl/diethylenetriamine copolymer.

(7) Cyclopolymers of alkyldiallylamine or of dialkyldiallylammonium, such as the homopolymers or copolymers comprising, as main constituent of the chain, units corresponding to the formulae (IX) or (X):

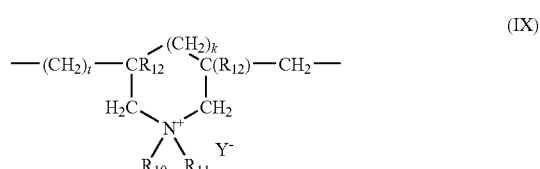

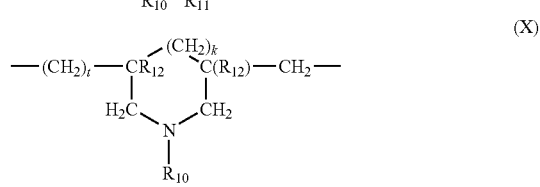

wherein k and t are equal to 0 or 1, the sum of k and t being equal to 1; $R_{12}$ is chosen from a hydrogen atom and a methyl group; $R_{10}$ and $R_{11}$ are chosen from, independently of one another, alkyl groups having from 1 to 6 carbon atoms, hydroxyalkyl groups comprising an alkyl group having 1 to 5 carbon atoms, a lower amidoalkyl group having a $C_1$-$C_4$ alkyl, or $R_{10}$ and $R_{11}$ can be chosen from, together with the nitrogen atom to which they are attached, a heterocyclic group such as piperidyl or morpholinyl; is an anion such as bromide, chloride, acetate, borate, citrate, tartrate, bisulphate, bisulphite, sulphate, or phosphate. These polymers may be the ones described in French Patent No. FR 2 080 759 and in its Certificate of Addition 2 190 406.

As a non-limiting example, $R_{10}$ and $R_{11}$ are chosen from, independently of one another, alkyl groups having from 1 to 4 carbon atoms.

Among the polymers defined above, non-limiting mention may be made of dialkyldiallylammonium chloride homopolymers, such as the dimethyldiallylammonium chloride homopolymer (INCI name: Polyquaternium-6) sold under the name MERQUAT® 100 by Nalco (and its homologues of low weight-average molecular weight) and dialkyldiallylammonium chloride copolymers, for instance, the copolymer of dimethyldiallylammonium chloride and of acrylamide sold under the name MERQUATO 550.

(8) Quaternary diammonium polymers comprising repeating units corresponding to the formula (XI):

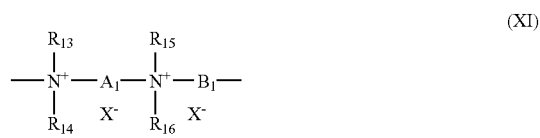

wherein:

$R_{13}$, $R_{14}$, $R_{15}$ and $R_{16}$, which may be identical or different, are chosen from aliphatic, alicyclic, and arylaliphatic groups comprising from 1 to 20 carbon atoms, and lower hydroxyalkylaliphatic groups (the alkyl part of which is a $C_1$-$C_4$alkyl); or alternatively $R_{13}$, $R_{14}$, $R_{15}$ and $R_{16}$, together or separately, form with the nitrogen atoms to which they are attached, at least one heterocycle optionally comprising a second heteroatom other than nitrogen; or alternatively $R_{13}$, $R_{14}$, $R_{15}$ and $R_{16}$ are chosen from linear or branched $C_1$-$C_6$ alkyl group substituted with at least one group chosen from nitrile, ester, acyl, amide, —CO—O—$R_{17}$-E, and, —CO—NH—$R_{17}$-E groups, where $R_{17}$ is chosen from alkylene groups and E is chosen from quaternary ammonium group;

$A_1$ and $B_1$ are chosen from linear or branched, saturated or unsaturated polymethylene groups comprising from 2 to 20 carbon atoms and optionally comprising, linked to or intercalated in the main chain, at least one aromatic ring or at least one group chosen from oxygen, sulphur, sulphoxide, sulphone, disulphide, amino, alkylamino, hydroxyl, quaternary ammonium, ureido, amide, and ester groups, and $X^-$ denotes an anion derived from an inorganic or organic acid;

$A_1$, $R_{13}$ and $R_{15}$ can form, with the two nitrogen atoms to which they are attached, a piperazine ring; or, in addition, if $A_1$ is chosen from a linear or branched, saturated or unsaturated alkylene and hydroxyalkylene group, $B_1$ can be chosen from a group:

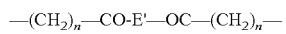

—$(CH_2)_n$—CO-E'—OC—$(CH_2)_n$— wherein n is chosen from an integer ranging from 0 to 7 and E' is chosen from:

a) a glycol residue of formula: —O—Z—O—, where Z is chosen from a linear or branched hydrocarbon-based group and groups corresponding to one of the following formulae:

—$(CH_2$—$CH_2$—O$)_x$—$CH_2$—$CH_2$—

—[$CH_2$—$CH(CH_3)$—O$]_y$—$CH_2$—$CH(CH_3)$— where x and y are chosen from an integer ranging from 1 to 4, which may represent a defined and unique degree of polymerization or may represent an average degree of polymerization;

b) a bis-secondary diamine residue such as a piperazine derivative;

c) a bis-primary diamine residue of formula: —NH—Y—NH—, wherein Y is chosen from linear or branched hydrocarbon-based groups and the divalent group of —$CH_2$—$CH_2$—S—S—$CH_2$—$CH_2$—; and d) a ureylene group of formula: —NH—CO—NH—.

For example, $X^-$ can be an anion such as chloride or bromide.

Polymers of this type may include but are not limited to those described in French Patent Nos. FR 2 320 330, FR 2 270 846, FR 2 316 271, FR 2 336 434, and FR 2 413 907, and U.S. Pat. Nos. 2,273,780, 2,375,853, 2,388,614, 2,454,547, 3,206, 462, 2,261,002, 2,271,378, 3,874,870, 4,001,432, 3,929,990, 3,966,904, 4,005,193, 4,025,617, 4,025,627, 4,025,653, 4,026,945, and 4,027,020.

Non-limiting mention may also be made of the polymers that are constituted of repeating units corresponding to the formula (XII):

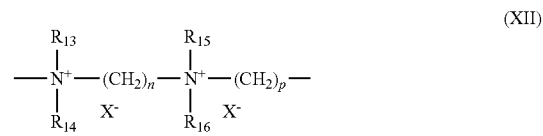

wherein $R_{13}$, $R_{14}$, $R_{15}$ and $R_{16}$, which may be identical or different, are chosen from alkyl and hydroxyalkyl groups having from 1 to 4 carbon atoms, n and p are integers ranging from 2 to 20, and $X^-$ is chosen from anions derived from an inorganic or organic acid. As a non-limiting example, $R_{13}$, $R_{14}$, $R_{15}$ and $R_{16}$ are chosen from methyl groups. By way of example of a polymer that corresponds to the formula (XII), non-limiting mention may be made of hexadimethrine chloride, sold under the name MEXOMERE PO by Chimex.

(9) Polyquaternary ammonium polymers comprising units of formula (XIII):

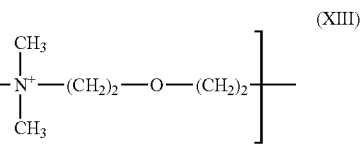

wherein:

p is chosen from an integer ranging from 1 to 6;

D may be absent or may be chosen from —$(CH_2)_r$—CO— groups, wherein r is chosen from a number equal to 4 or to 7, and $X^-$ is chosen from anions derived from an inorganic or organic acid.

The cationic polymers comprising units of formula (XIII) may be the ones described in, for example, European Patent Application No. EP-A-122 324, and may be the ones prepared according to the processes described in U.S. Pat. Nos. 4,157,388, 4,390,689, 4,702,906, and 4,719,282.

Among these polymers, non-limiting mention may be made of those having a molecular weight measured by Carbon-13 NMR of less than 100,000, and in the formula of which:

p is equal to 3, and, a) D is a —$(CH_2)_4$—CO— group, X is chosen from a chlorine atom, the molecular weight measured by Carbon-13 NMR ($^{13}$C NMR) being around 5600; a polymer of this type is proposed by Miranol under the name MIRAPOL-AD1, b) D is a —$(CH_2)_7$—CO— group, X is chosen from a chlorine atom, the molecular weight measured by Carbon-13 NMR ($^{13}$C NMR) being around 8100; a polymer of this type is proposed by Miranol under the name MIRAPOL-AZ1, c) D is chosen from the value zero, X is chosen from a chlorine atom, the molecular weight measured by Carbon-13 NMR ($^{13}$C NMR) being around 25,500; a polymer of this type is sold by Miranol under the name MIRAPOL-A15, d) a "block copolymer" formed from units corresponding to the polymers described in paragraphs a) and c), proposed by Miranol under the names MIRAPOL-9 ($^{13}$C NMR molecular weight, around 7800), MIRAPOL-175 ($^{13}$C NMR molecular weight, around 8000) and MIRAPOL-95 ($^{13}$C NMR molecular weight, around 12,500).

Further as a non-limiting example, according to the present disclosure, the polymer having units of formula (XIII), wherein p is equal to 3, D is chosen from the value zero, X is chosen from a chlorine atom, the molecular weight measured by Carbon-13 NMR ($^{13}$C NMR) being around 25,500, may be used.

(10) Quaternary polymers of vinylpyrrolidone and of vinylimidazole such as, for example, the products sold under the names LUVIQUAT FC 905, FC 550 and FC 370 by BASF.

(11) Cationic polyamines such as POLYQUART H sold by Henkel, referenced under the name "POLYETHYLENE GLYCOL (15) TALLOW POLYAMINE" in the CTFA dictionary.

(12) Homopolymers or copolymers of vinylamide, for example, partially hydrolyzed homopolymers of vinylamide such as poly(vinylamine/vinylamide)s. These polymers are formed from at least one vinylamide monomer corresponding to the following formula:

wherein R, $R^1$ and $R^2$ are each chosen from a hydrogen atom, $C_1$-$C_{20}$ alkyl groups, aryl groups, and alkylaryl groups, the alkyl part of which comprises from 1 to 20 carbon atoms.

As a non-limiting example, said monomer may be chosen from N-vinylformamide, N-methyl-N-vinylacetamide, and N-vinyl acetamide. For instance, poly(vinylamine/N-vinylformamide) is used, as sold under the name CATIOFAST VMP by BASF or under the name LUPAMIN 9030 by BASF.

These polymers may be formed, for example, by radical polymerization of a vinylamide monomer then partial acid or basic hydrolysis of the amide functional groups to quaternizable amine functional groups, such as the ones described in International Patent Application Nos. WO 2007/005577, and U.S. Pat. Nos. 5,374,334, 6,426,383 and 6,894,110.

(13) Polyurethanes comprising:
(a1) at least one cationic unit derived from at least one tertiary or quaternary amine having at least two reactive functional groups comprising labile hydrogen,
(a2) at least one non-ionic unit derived from at least one polyolefin having at least two reactive functional groups comprising labile hydrogen, the at least one polyolefin comprising at least 10 mol % of units comprising at least one C=C (carbon-carbon) double bond, relative to the total amount of units forming the at least one polyolefin; and
(b) at least one unit derived from a compound comprising at least two isocyanate functional groups.

In some embodiments, the polymer according to the present disclosure may be of elastic nature; this means that said polymer is a macromolecular material that rapidly returns to its initial form and dimensions after a low stress that has produced a large deformation has been removed.

These polymers may be obtained by polycondensation of compounds bearing reactive functional groups comprising labile hydrogen with compounds comprising at least two isocyanate functional groups.

As used herein, the term "reactive functional groups comprising labile hydrogen" means functional groups capable, after loss of a hydrogen atom, of forming covalent bonds with the isocyanate functional groups of compounds comprising at least two isocyanate functional groups. Non-limiting examples of such functional groups include hydroxyl, primary amine or secondary amine groups, or thiol groups.

Depending on the nature of the reactive functional groups bearing the labile hydrogen (—OH, —NH$_2$, —NHR or —SH), the polycondensation leads, respectively, to polyurethanes, polyureas or polythiourethanes. Thus, the polymers that can be used in the compositions according to the present disclosure may be urethane/urea and/or thiourethane copolymers. All these polymers may be referred to as, for the sake of simplicity, the term "polyurethanes".

The cationic polyurethane(s) that can be used in the composition according to the present disclosure thus comprise at least one cationic unit (a1) resulting from at least one tertiary or quaternary amine having at least two reactive functional groups comprising labile hydrogen.

The tertiary amine may be protonatable at a pH ranging from pH 1 to pH 12. The term "protonatable" means that said tertiary amine functional group may be at least partially neutralized with a neutralizer or by a functional group of the medium in which it is formulated.

When the tertiary or quaternary amines forming the units (a1) bear more than two functional groups comprising labile hydrogen, the polyurethanes obtained have a branched structure.

However, as an example, when the tertiary or quaternary amines forming the units (a1) have only two reactive functional groups comprising labile hydrogen, the polyurethanes thus obtained via polycondensation may have an essentially linear structure.

It is also possible to use a mixture of difunctional amines comprising, or otherwise, a small proportion of amines bearing more than two reactive functional groups comprising labile hydrogen.

The tertiary or quaternary amines forming the cationic units (a1) may be chosen from compounds corresponding to at least one of the following formulae:

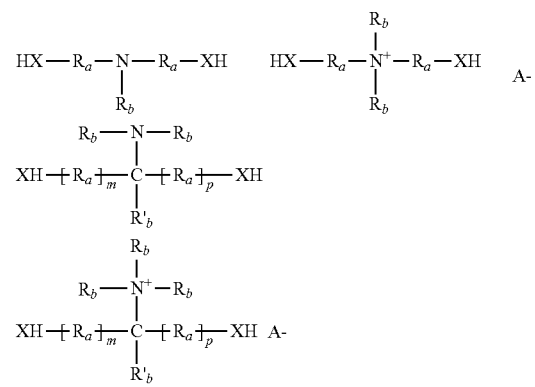

-continued

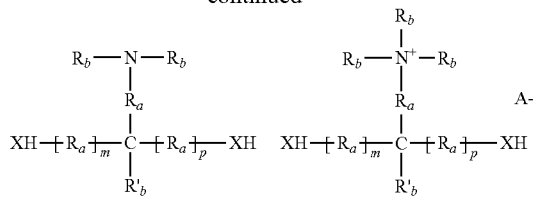

wherein:
each $R_a$, independently of one another, is chosen from linear and branched divalent $C_1$-$C_6$ alkylene groups, $C_3$-$C_6$ cycloalkylene groups, and arylene groups; these groups possibly being substituted with at least one halogen atom and/or comprising at least one heteroatom chosen from O, N, P, and S;
each $R_b$ is chosen from, independently of one another, linear and branched $C_1$-$C_6$ alkyl groups, $C_3$-$C_6$ cycloalkyl groups, and aryl groups; these groups possibly being substituted with at least one halogen atoms and/or comprising at least one heteroatoms chosen from O, N, P, and S;
each $R'_b$ is chosen from a hydrogen atom, linear and branched $C_1$-$C_6$ alkyl groups, $C_3$-$C_6$ cycloalkyl groups, and aryl groups; these groups possibly being substituted with at least one halogen atom and/or comprising at least one heteroatom chosen from O, N, P, and S;
m and p are, independently of one another, equal to 0 or 1; such as m=1 and p=1;
each X is chosen from, independently of one another, oxygen, sulphur, NH, and $NR_c$ groups, where $R_c$ is chosen from $C_1$-$C_6$ alkyl groups; and
$A^-$ is chosen from physiologically acceptable counterions, for example a halide such as chloride or bromide.
As non-limiting examples, the amines are chosen from the compounds corresponding to at least one of the formulae:

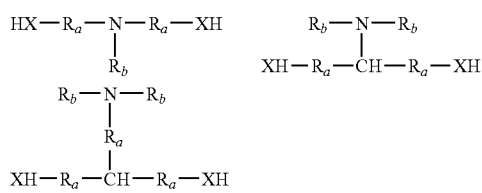

wherein:
$R_a$ is chosen from linear and branched divalent $C_1$-$C_6$ alkylene groups, such as methylene or ethylene; and/or
$R_b$ is chosen from linear and branched $C_1$-$C_6$ alkyl groups, for example, a methyl, ethyl, n-butyl, isobutyl, or tart-butyl group; and/or
X is chosen from an oxygen atom.
Further as a non-limiting example, the amines are of formula:

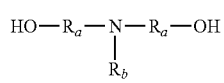

wherein $R_a$ is chosen from linear and branched divalent $C_1$-$C_6$ alkylene groups, such as methylene or ethylene;

and $R_b$ is chosen from linear and branched $C_1$-$C_6$ alkyl groups, for instance, a methyl, ethyl, n-butyl, isobutyl, or tert-butyl group.

Additional examples of tertiary amines include but are not limited to, N-methyldiethanolamine and N-tert-butyldiethanolamine.

The protonatable tertiary amines may be totally or partially neutralized with a neutralizer of organic acid type comprising at least one functional group chosen from carboxylic, sulphonic, and phosphoric acid functional groups, or with an inorganic acid. Non-limiting examples of acids that may be mentioned include hydrochloric acid, sulphuric acid, acetic acid, propionic acid, citric acid, gluconic acid, tartaric acid, lactic acid, phosphoric acid, benzoic acid, stearic acid, oleic acid, 2-ethylcaproic acid, behenic acid, and betaine hydrochloride, and mixtures thereof.

The cationic polyurethane(s) that can be used in the composition according to the present disclosure also comprise at least one non-ionic unit (a2) resulting from at least one polyolefin having at least two reactive functional groups comprising labile hydrogen, said polyolefin comprising at least 10 mol % of units comprising at least one (residual) C=C double bond, relative to the total amount of units forming said polyolefin.

As a non-limiting example, the polyolefin(s) is (are) non-ionic.

Further as a non-limiting example, the reactive functional groups comprising labile hydrogen are located at the ends of the polyolefin. Said reactive functional groups comprising labile hydrogen may be, for example, hydroxides. In addition, as an example, the number of hydroxide units is close to or equal to 2.

Yet as another example, the polyolefin(s) forming the unit (a2) is chosen from olefin homopolymers and/or copolymers, bearing at their ends reactive functional groups comprising labile hydrogen and having a glass transition temperature ($T_g$), measured by differential thermal analysis (DSC, differential scanning calorimetry) according to the ASTM D3418-97 standard, of less than 10° C.

The polyurethane(s) in the composition according to the present disclosure may comprise several units (a2) resulting from several identical or different polyolefins (polyolefin blends); however, in this case, each of the polyolefins comprises at least 10 mol % of units comprising at least one C=C double bond.

As used herein, the term "unit comprising a C=C double bond" means a unit comprising at least one residual C=C double bond, for instance, only one double bond; it may be, for example, a unit derived from the polymerization of a butadiene or isoprene unit, all isomeric forms included (cis or trans, 1,2- or 1,4-).

The polyolefin that can be used may be an olefin homopolymer. Non-limiting mention may be made, for example, of homopolymers of 1,2-butadiene, of 1,4-butadiene, or of isoprene, and for instance:

1,4-polybutadienes, in their cis and trans forms:

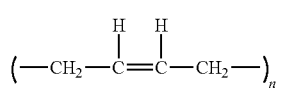

poly(1,2-butadiene)s:
[CH$_2$—CH(CH=CH$_2$)—]$_n$
poly(cis-1,4-isoprene)s:

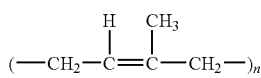

poly(trans-1,4-isoprene)s:

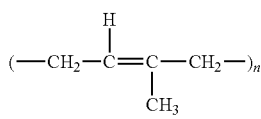

The polyolefin that can be used may also be a copolymer of various olefins (olefin copolymer), provided that the final polyolefin comprises at least 10 mol % of units comprising at least one C=C double bond.

In some embodiments, said polyolefin may be exclusively constituted of units comprising at least one C=C double bond. Non-limiting mention may be made, for example, of the copolymers, such as statistical copolymers, comprising 1,2-butadiene units and/or 1,4-butadiene units in their cis and/or trans forms, and/or isoprene units, for example, cis-1, 4-isoprene and trans-1,4-isoprene, as a mixture. Non-limiting mention may also be made of (1,2-butadiene/1,4-butadiene) statistical copolymers.

As non-limiting examples, the polyolefin(s) that can be used may be statistical with hydroxyl end groups and correspond to the following structure:

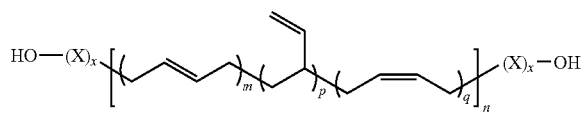

wherein:

m, p, and q are mole fractions ranging from 0 to 1, and m+p+q=1; for instance, with m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;

n is an integer ranging from 10 to 100, such as from 15 to 50;

x=0 or 1; and

X is chosen from divalent carbon-based groups, such as a linear, cyclic, or branched alkylene group, comprising from 1 to 10 carbon atoms; such as, for example, a methylene, ethylene, propylene, or isopropylene group.

They may have, for example, a number-average molecular weight, $M_n$; ranging from 400 to 50,000, such as from 500 to 30,000, or for instance, from 1000 to 15,000 such as from 1500 to 12,000.

Non-limiting mention may be made of:

polybutadienes with hydroxyl end groups, such as the polymers of structure:

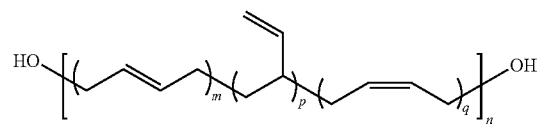

with m=0.6, p=0.2 and q=0.2 (mole fractions) and n=25.

Non-limiting mention may be made of the commercial products POLY BD R20LM and POLY BD R45HTLO from Sartomer.

polybutadienes with primary hydroxyl end groups, such as the polymers that may be represented by the following structure:

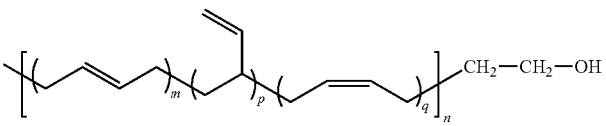

which may be statistical copolymers such as of cis-1,4-butadiene and of trans-1,4-butadiene, with m=0.17, p=0.65 and q=0.18 (mole fractions) and n is such that the number-average molecular weight $M_n$ ranges from 1000 to 10,000 such as from 2000 to 6000 (g/mol).

Non-limiting mention may be made of the commercial products KRASOL LBH-P 2000, 3000 or 5000 from Sartomer.

polybutadienes with secondary hydroxyl end groups, such as the polymers that may be represented by the following structure:

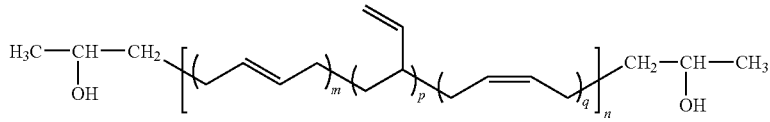

which may be statistical copolymers of cis-1,4-butadiene and of trans-1,4-butadiene, with m=0.17, p=0.65 and q=0.18 (mole fractions), and n is such that the number-average molecular weight $M_n$ varies from 1000 to 12,000 such as from 2000 to 10,000 (g/mol).

Non-limiting mention may be made of the commercial products KRASOL LBH 2000, 3000, 5000 or 10 000 from Sartomer.

In some embodiments, said polyolefin(s) may also comprise additional units not comprising a C=C double bond.

However, these additional units are present in a maximum amount of 90 mol %, given that the final polyolefin should comprise at least 10 mol % of units comprising at least one C=C double bond.

These additional olefin units may be chosen from, for instance, ethylene —(CH$_2$—CH$_2$)$_n$—, propylene —(CH$_2$—CH$_2$—CH$_2$)$_n$—, isopropylene —(CH$_2$CH(CH$_3$))$_n$— units, and/or butylene units of formula:

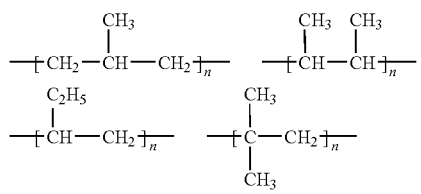

and also mixtures thereof.

The olefin homopolymers or copolymers as defined above may undergo, after polymerization, a partial hydrogenation of the residual double bonds. This hydrogenation cannot in any way lead to a complete hydrogenation of the olefin homopolymers or copolymers.

As non-limiting examples, the polyolefin(s) that may be used to form the units (a2) according to the present disclosure should necessarily comprise at least 10 mol % of units comprising at least one (residual) C=C double bond, relative to the total amount of units forming said polyolefin.

For instance, they may comprise at least 20 mol %, for example, at least 40 mol %, or even at least 50 mol %, such as at least 80 mol % or such as 100 mol %, of units comprising at least one C=C double bond, for example, units comprising only one C=C double bond.

The amount of units comprising at least one C=C double bond may be determined via the known techniques, such as via NMR or iodine assay.

As a non-limiting example, the polyolefin(s) that can be used to form the non-ionic units (a2) may have a number-average molecular weight ($M_n$) ranging from 400 to 50,000, such as from 500 to 30,000, or for instance, from 1000 to 15,000 such as from 1500 to 12,000.

In some embodiments, the polyolefin(s) that may be used in the context of the present disclosure may be chosen from:
homopolymers such as poly(1,4-butadiene) and poly(1,2-butadiene);
copolymers of structure:

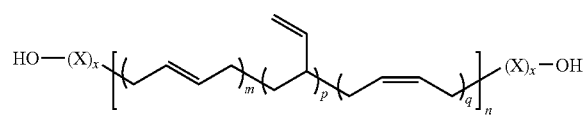

wherein:
m, p and q are mole fractions ranging from 0 to 1, and m+p+q=1; for instance, with m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;
n is an integer ranging from 10 to 100, such as from 15 to 50;
x=0 or 1; and
X is chosen from divalent carbon-based groups, such as linear, cyclic, or branched alkylene groups, comprising from 1 to 10 carbon atoms; such as, for example, a methylene, ethylene, propylene, or isopropylene group.

The cationic polyurethane(s) that can be used in the composition according to the present disclosure may further comprise at least one unit (b) resulting from at least one compound comprising at least two isocyanate functional groups.

It may also be a mixture of several compounds comprising at least two isocyanate functional groups.

The compounds comprising at least two isocyanate functional groups may be chosen from diisocyanates, or mixtures of a diisocyanate and a polyisocyanate comprising more than two isocyanate functional groups, said polyisocyanate may be in an amount ranging from 0.1% to 40% by weight of said mixture, such as ranging from 0.5% to 35% by weight or even ranging from 1% to 30% by weight of the weight of said mixture.

The compounds comprising at least two isocyanate functional groups may be chosen from, for instance, conjugated or non-conjugated, aromatic or non-aromatic, cyclic, aliphatic diisocyanates. They may be chosen from, for example, methylenediphenyl diisocyanate, methylenecyclohexane diisocyanate, isophorone diisocyanate, toluene diisocyanate, naphthalene diisocyanate, 1,4-butane diisocyanate and 1,6-hexane diisocyanate, and a mixture thereof; such as isophorone diisocyanate.

As a non-limiting example, the polyurethane(s) that can be used in the composition according to the present disclosure may be essentially constituted of:

at least one cationic unit resulting from amines of formula:

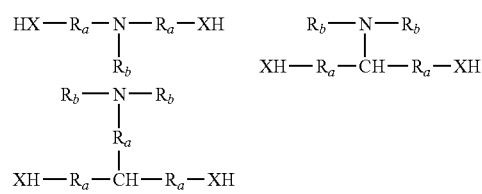

wherein:
$R_a$ is chosen from linear or branched divalent $C_1$-$C_6$ alkylene groups, such as a methylene or ethylene group;
$R_b$ is chosen from linear or branched $C_1$-$C_6$ alkyl groups, such as chosen from methyl, ethyl, n-butyl, isobutyl, and tert-butyl groups; and
X is chosen from a hydrogen atom;
at least one non-ionic unit resulting from polyolefins chosen from poly(1,4-butadiene) and poly(1,2-butadiene) homopolymers; or copolymers of structure:

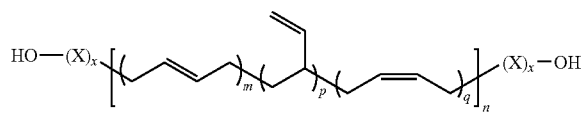

wherein:
m, p and q are mole fractions ranging from 0 to 1, and m+p+q=1; for instance, with m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;

n is an integer ranging from 10 to 100, such as from 15 to 50;

x=0 or 1; and

X is chosen from divalent carbon-based groups, such as a linear, cyclic or branched alkylene group, comprising from 1 to 10 carbon atoms; such as, for example, a methylene, ethylene, propylene, or isopropylene group;

at least one unit resulting from aliphatic diisocyanates.

Further as non-limiting examples, the polyurethane(s) that can be used according to the present disclosure may be essentially constituted of:

at least one cationic unit resulting from amines of formula:

$$HO-R_a-N(R_b)-R_a-OH$$

wherein $R_a$ is chosen from linear or branched divalent $C_1$-$C_6$ alkylene groups, such as a methylene or ethylene group; and $R_b$ is chosen from linear or branched $C_1$-$C_6$ alkyl groups, for instance, a methyl, ethyl, n-butyl, isobutyl, or tert-butyl group;

or as an example, at least one cationic unit chosen from N-methyldiethanolamine and N-tert-butyldiethanolamine;

at least one non-ionic unit resulting from polyolefins of structure:

$$HO-(X)_x-[[-\text{(diene units)}_m-\text{(vinyl)}_p-\text{(diene)}_q-]_n-(X)_x-OH$$

wherein:

m, p and q are mole fractions ranging from 0 to 1, and m+p+q=1; for instance, with m ranging from 0.1 to 0.8, or even from 0.15 to 0.7; p ranging from 0.1 to 0.8, or even from 0.15 to 0.7; and q ranging from 0.05 to 0.5, or even from 0.1 to 0.4;

n is an integer ranging from 10 to 100, such as from 15 to 50;

x=0 or 1; and

X is chosen from divalent carbon-based groups, such as a linear, cyclic, or branched alkylene group, comprising from 1 to 10 carbon atoms; such as, for example, a methylene, ethylene, propylene, or isopropylene group;

at least one unit resulting from diisocyanates chosen from methylenecyclohexane diisocyanate, isophorone diisocyanate, 1,4-butane diisocyanate, and 1,6-hexane diisocyanate; such as isophorone diisocyanate.

In some embodiments, the polyurethanes that can be used according to the present disclosure may be essentially constituted of units (a1), (a2) and (b) as defined above, which implies that it does not comprise additional units other than these.

In some embodiments, the polyurethanes may be chosen from the polyurethanes formed from the following monomers:

(a1) at least one N-methyldiethanolamine (denoted by NMDEA), (a2) at least one non-ionic ethylene/butylene copolymer as sold under the name KRASOL LBH-P 2000, and (b) at least one isophorone diisocyanate (denoted by IPDI).

In some embodiments, the amines that form the cationic units (a1) is present in an amount ranging from 0.1% to 50%, such as from 1% to 30%, or for example, from 5% to 20% by weight, of the total weight of the final polyurethane.

In some embodiments, the polyolefins that form the non-ionic units (a2) are present in an amount ranging from 30% to 99% by weight, for example, from 50% to 90%, and such as from 60% to 80% by weight, of the total weight of the final polyurethane.

In some embodiments, the compounds comprising at least two isocyanate functional groups, which form the units (b), are present in an essentially stoichiometric amount relative to the sum of the tertiary/quaternary amines that form the units (a1) and of the polyolefins that form the units (a2).

In some embodiments, the compounds comprising at least two isocyanate functional groups, which form the units (b), are present in an amount ranging from 0.1% to 60% by weight, for instance, from 5% to 50% by weight, such as from 15% to 35% by weight, of the total weight of the final polyurethane.

Further as non-limiting examples, the polyurethanes according to the present disclosure may be formed from:

20 mol % to 55 mol %, for example, from 25 mol % to 50 mol %, or even from 30 mol % to 47 mol % of tertiary or quaternary amine capable of forming the units (a1);

1 mol % to 30 mol %, for instance, from 2 mol % to 25 mol %, or even from 3 mol % to 20 mol % of polyolefin capable of forming the units (a2); and 30 mol % to 65 mol %, for example, 35 mol % to 60 mol %, or even from 45 mol % to 55 mol % of compound comprising at least two isocyanate functional groups capable of forming the units (b).

In some embodiments, the molar ratio between (b) and (a1)+(a2) is close to 1.

These polyurethanes and the syntheses thereof may be the one described, for example, in French Patent Application No. FR-A-289 8 603.

(14) Other cationic polymers that can be used in the context of the present disclosure include cationic proteins or cationic protein hydrolysates, polyalkyleneimines, such as polyethyleneimines, polymers comprising vinylpyridine or vinylpyridinium units, and chitin derivatives.

In some embodiments, the at least one cationic polymer E is chosen from the cationic polymers chosen from cyclic homopolymers of alkyldiallylamine or of dialkyldiallylammonium from the family (7), cationic homopolymers and copolymers of vinylamine from the family (12), and polyurethanes from the family (13); for instance, the at least one cationic polymer E is poly(vinylamine/N-vinylformamide).

The at least one cationic polymer E is present in an amount ranging from 0.01% to 10% by weight, such as from 0.05% to 8% by weight, for instance, from 0.1% to 5% by weight, relative to the total weight of the composition.

Zinc Salt (F)

As used herein, the term "zinc salt" is understood to mean any inorganic or organic compound comprising, in its structure, at least one zinc atom.

In some embodiments, the at least one zinc salt (F) used according to the present disclosure may be chosen from water-soluble zinc salts.

As used herein, the term "water-soluble zinc salt" is understood to mean any salt having a water solubility of greater than or equal to 0.5% by weight at a temperature of 25° C.

Among the water-soluble zinc salts that can be used according to the present disclosure, non-limiting mention may be made of zinc sulphate, zinc chloride, zinc lactate, zinc gluconate, zinc phenolsulphonate, zinc salicylate, derivatives thereof, and mixtures thereof.

Zinc salicylate and its derivatives according to the present disclosure correspond to the structure (XIV) below:

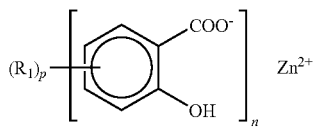

(XIV)
wherein:
n=2, p is chosen from 0, 1, 2, and 3;

$R_1$ is chosen from linear and branched $C_1$-$C_{18}$ alkyl groups (for example, methyl, ethyl, n-propyl, isopropyl, or n-butyl); linear and branched $C_1$-$C_{18}$ hydroxyalkyl groups; halogen atoms (for example, iodine, bromine, or chlorine); $C_2$-$C_{18}$ acyl groups (for example, acetyl); $COR_2$, $OCOR_2$, and $CONHR_2$ groups; wherein $R_2$ is chosen from hydrogen atom and linear and branched $C_1$-$C_{18}$ alkyl groups.

In some embodiments, the at least one zinc salt (F) is chosen from zinc sulphate, zinc chloride, and zinc gluconate; for example, the compound sold, for example, under the name GIVOBIO G Zn by SEPPIC.

In some embodiments, the at least one zinc salt (F) of the present disclosure is chosen from inorganic salts.

The term "inorganic zinc salt", is understood to mean any zinc salt that optionally only comprises carbon in the form chosen from carbonate ions and hydrogen carbonate ions.

The at least one zinc salt (F) according to the present disclosure may be present in the composition in an amount ranging from 0.005% to 30% by weight, such as from 0.1% to 20% by weight, or for example, from 0.3% to 15% by weight, relative to the total weight of the composition.

In some embodiments, the zinc element of the at least one zinc salt (F) is present in an amount of less than 2% by weight, such as ranging from 0.005% to 1.5% by weight, or for example, from 0.1% to 1% by weight, relative to the total weight of the composition.

In some embodiments, the at least one zinc salt (F) according to the present disclosure may be present in the composition in an amount such that the weight ratio of the amount of anionic, amphoteric and/or zwitterionic, and non-ionic surfactant(s) to the amount of zinc element of the at least one zinc salt (F) has a value greater than 2, for example, greater than or equal to 5. Further as an example, the value of the weight ratio ranges from 10 to 25.

Ultraviolet Screening Agent (G)

When the composition according to the present disclosure comprises at least one UV-screening agent (systems that screen out ultraviolet radiation), the at least one UV-screening agent is chosen from organic and inorganic UV-screening agents, such as organic UV-screening agents.

The organic UV-screening agent that can be used according to the present disclosure, may be chosen from water-soluble or liposoluble, silicone or non-silicone screening agents.

The term "water-soluble screening agent" is understood to mean any UV-screening agent that is soluble in water, such as having a solubility of 0.5% by weight in water at 25° C.

The organic UV-screening agents may be chosen from, for example:
dibenzoylmethane derivatives;
anthranilates;
cinnamic derivatives;
salicylic derivatives;
camphor derivatives;
benzophenone derivatives;
β,β-diphenylacrylate derivatives;
triazine derivatives;
benzotriazole derivatives;
benzalmalonate derivatives;
benzimidazole derivatives;
imidazolines;
bisbenzoazolyl derivatives, as described in European Patent No. EP 669 323 and U.S. Pat. No. 2,463,264;
p-aminobenzoic acid (PABA) derivatives;
benzoxazole derivatives, as described in European Patent applications No. EP 0 832 642, EP 1 027 883, and EP 1 300 137, and German Patent Application No. DE 10 162 844;
screening polymers and screening silicones, such as those described in International Patent Application Publication No. WO 93/04665;
dimers derived from α-alkylstyrene, such as those described in German Patent Application No. DE 19 855 649; and
4,4-diarylbutadienes, such as those described in European Patent Application Nos. EP 0 967 200, EP 1 008 586, EP 1 133 980 and EP 133 981; and German Patent Application Nos. DE 19 746 654, and DE 19 755 649.

As examples of organic UV screening agents, non-limiting mention may be made of those compounds described under their INCI name:

Para-Aminobenzoic Acid Derivatives:
p-Aminobenzoic acid (PABA),
Ethyl PABA,
Ethyl dihydroxypropyl PABA,
Ethyhexyl dimethyl PABA sold, for example, under the name ESCALOL 507 by ISP,
Glyceryl PABA,
PEG-25 PABA sold under the name UVINUL P25 by BASF.

Cinnamic Derivatives:
Ethylhexyl methoxycinnamate sold, for instance, under the trade name PARSOL MCX by Hoffmann LaRoche,
Isopropyl methoxycinnamate,
Isoamyl methoxycinnamate sold under the trade name NEO HELIOPAN E 1000 by Haarmann and Reimer,
Cinoxate,
Diethanolamine methoxycinnamate,
Diisopropyl methylcinnamate,
Glyceryl ethylhexanoate dimethoxycinnamate.

Dibenzoylmethane Derivatives:
Butylmethoxydibenzoylmethane sold, for example, under the trade name PARSOL 1789 by Hoffmann LaRoche,
Isopropyldibenzoylmethane sold, for instance, under the trade name EUSOLEX 8020 by Merck.

Salicylic Derivatives:
Homosalate sold under the name EUSOLEX HMS by Rona/EM Industries, Ethylhexyl salicylate sold under the name NEO HELIOPAN OS by Haarmann and Reimer,
Dipropylene glycol salicylate sold under the name DIPSAL by Scher,
Triethanolamine salicylate sold under the name NEO HELIOPAN TS by Haarmann and Reimer.)

β,β-Diphenylacrylate Derivatives:
Octocrylene sold, for instance, under the trade name UVINUL N539 T by BASF,
Etocrylene sold, for example, under the trade name UVINUL N35 by BASF.
Benzophenone Derivatives:
Benzophenone-1 sold under the trade name UVINUL 400 by BASF,
Benzophenone-2 sold under the trade name UVINUL D50 by BASF,
Benzophenone-4 sold under the trade name UVINUL MS40 by BASF,
Benzophenone-5,
Benzophenone-6 sold under the trade name HELISORB 11 by Norquay,
Benzophenone-8 sold under the trade name SPECTRA-SORB UV-24 by American Cyanamid,
Benzophenone-9 sold under the trade name UVINUL DS-49 by BASF,
Benzophenone-12,
n-hexyl 2-(4-diethylamino-2-hydroxybenzoyl)benzoate.
Benzylidenecamphor Derivatives:
3-Benzylidenecamphor manufactured under the name MEXORYL SD by Chimex,
4-Methylbenzylidenecamphor sold under the name EUSOLEX 6300 by Merck,
Benzylidenecamphorsulphonic acid manufactured under the name MEXORYL SL by Chimex,
Camphor benzalkonium methosuiphate manufactured under the name MEXORYL SO by Chimex,
Terephthalylidenedicamphorsulphonic acid manufactured under the name MEXORYL SX by Chimex,
Polyacrylamidomethylbenzylidenecamphor manufactured under the name MEXORYL SW by Chimex.
Phenylbenzimidazole Derivatives:
Phenylbenzimidazolesulphonic acid sold for example, under the trade name EUSOLEX 232 by Merck,
Disodium phenyl dibenzimidazole tetrasulphonate sold under the trade name NEO HELIOPAN AP by Haarmann and Reimer.
Phenylbenzotriazole Derivatives:
Drometrizole trisiloxane sold under the name SILATRIZOLE by Rhodia,
Methylenebis(benzotriazolyl)tetramethylbutylphenol sold in solid form under the trade name MIXXIM BB/100 by Fairmount Chemical, or in micronized form as an aqueous dispersion under the trade name TINOSORB M by Ciba Specialty Chemicals.
Triazine Derivatives:
Bisethylhexyloxyphenol Methoxyphenyl Triazine sold under the trade name TINOSORB S by Ciba Geigy,
Ethylhexyltriazone sold, for example, under the trade name UVINUL T150 by BASF,
Diethylhexylbutamidotriazone sold under the trade name UVASORB HEB by Sigma 3V,
2,4,6-tris(diisobutyl 4'-aminobenzalmalonate)-s-triazine.
Anthranilic Derivatives:
Menthyl anthranilate sold under the trade name NEO HELIOPAN MA by Haarmann and Reimer.
Imidazoline Derivatives:
Ethylhexyldimethoxybenzylidenedioxoimidazoline propionate.
Benzalmalonate Derivatives:
Polyorganosiloxane comprising benzalmalonate functional groups, for instance, Polysilicone-15, sold under the trade name PARSOL SLX by Hoffmann LaRoche,
Diethyl syringylidene malonate sold, for example, under the trade name OXYNEX ST by Merck.
4,4-Diarylbutadiene Derivatives:
1,1-Dicarboxy(2,2'-dimethylpropyl)-4,4-diphenylbutadiene.
Benzoxazole Derivatives:
2,4-bis[5-(1-dimethylpropyl)benzoxazol-2-yl-(4-phenyl)imino]-6-(2-ethylhexyl)imino-1,3,5-triazine sold under the trade name UVASORB K2A by Sigma 3V.

In some embodiments, liposoluble (or lipophilic) organic UV screening agents that may be suitable for use in the present disclosure include but not limited to:
benzophenone derivatives;
β,β-diphenylacrylate derivatives;
benzalmalonate derivatives;
triazine derivatives;
phenylbenzotriazole derivatives;
dibenzoylmethane derivatives;
benzylidenecamphor derivatives;
and mixtures thereof.

The at least one UV screening agent (G), if present, is present in an amount ranging from 0.01% to 20% by weight, such as from 0.5% to 15% by weight, or for example, from 1% to 10% by weight, relative to the total weight of the composition.

In some embodiments, the composition of the present disclosure does not comprise UV-screening agent.

The composition according to the present disclosure may have a pH ranging from 3 to 8, for instance, a pH ranges from 4 to 7.5. The adjustment of the pH to the desired value may be carried out by the addition of at least one (organic or inorganic) base into the composition, for example sodium hydroxide, aqueous ammonia, or a primary, secondary or tertiary (poly)amine such as monoethanolamine, diethanolamine, triethanolamine, isopropanolamine or 1,3-propanediamine, or else by the addition of at least one organic or inorganic acid, such as the citric acid or hydrochloric acid.

The composition according to the present disclosure may comprise at least one cosmetically acceptable medium.

The at least one cosmetically acceptable medium may be an aqueous medium constituted solely of water or of a mixture of water and at least one cosmetically acceptable solvents, such as a $C_1$-$C_4$ lower alcohol, (for instance ethanol, isopropanol, ten-butanol or n-butanol); alkylene glycols (for instance propylene glycol or hexylene glycol); glycerol; or mixtures thereof.

In some embodiments, the composition according to the present disclosure may comprises at least 30% by weight of water, for example, from 50% to 90% by weight and such as from 70% to 85% by weight, relative to the total weight of the composition.

The composition according to the present disclosure may further comprise, in addition to the compounds (A), (B), (C), (D), (E) and (F) as defined previously, at least one additive.

The term "additive" is understood to mean a compound other than the compounds (A), (B), (C), (D), (E) and (F) used according to the present disclosure, added to a composition of the present disclosure. For example, when the composition according to the present disclosure comprises at least one UV-screening agents (G) and also comprises at least one additive, said at least one additive being different from said UV-screening agent(s) (G).

Among the additives that can be used, non-limiting mention may be made of the conventional additives that are known in the art, such as non-ionic surfactants other than those of the present disclosure, cationic surfactants, anti-dandruff agents, agents for combating hair loss, ceramides and pseudoceramides, vitamins and provitamins including panthenol, plant, animal, mineral or synthetic oils, waxes, mineral or organic, colored or uncolored pigments, dyes, pearlescent agents, opacifiers, sequestrants, plasticizers, solubilizing agents, acidifying agents, basifying agents, inorganic or organic thickeners, stabilizers, antioxidants, free-radical scavengers, fragrances, preservatives, or mixtures thereof.

As a non-limiting example, the stabilizers may be chosen from tris(tetra-methylhydroxypiperidinol)citrate sold under the trade name TINOGARD Q by CIBA.

The at least one additive may be present in an amount ranging from 0% to 20% by weight, relative to the total weight of the composition.

A person skilled in the art will take care to select the optional at least one additive and the amount thereof such that it does not harm the properties of the compositions of the present disclosure.

Another aspect of the present disclosure relates to a process for washing and/or cleansing keratin fibers, for example, human keratin fibers, such as the hair, or such as colored hair, which comprises the application, to said keratin fibers, of an effective amount of a cosmetic composition according to the present disclosure.

The composition may be applied to dry or wet hair, such as to wet or damp hair.

In some embodiments, such a process comprises applying to the hair an effective amount of the composition according to the present disclosure, optionally kneading the hair, optionally leaving the composition on the hair, and rinsing the hair.

When said composition is left on the hair, the leave-in time may range from 0.5 to 5 minutes. The composition may be rinsed off with water.

Another aspect of the present disclosure is a multi-compartment kit comprising at least one compartment comprising at least one dyeing composition chosen from one-part and two-part oxidation dye and direct dye compositions, and at least one compartment comprising a cosmetic composition according to the present disclosure.

The following examples are given by way of illustration of the present disclosure, and should not limit the scope thereof.

EXAMPLES

Dyeing Step

The following dyed locks were prepared.

At the time of use, the commercial dye MAJIREL® 6.1 (dark ash blonde) was mixed with an equal amount in weight of aqueous hydrogen peroxide solution (at 20 volumes).

The mixture was then applied to permed locks of hair containing 90% white hair in an amount of 15 g of dye mixture per gram of hair locks. After a leave-in time of 15 minutes, the hair locks were washed with a commercial DOP shampoo and were dried for 30 minutes under a hood at 60° C.

Shampooing:

The following shampoo compositions A to G were prepared. The amounts are indicated in percent by weight of active material (AM) relative to the total weight of the composition.

|  | Shampoo | | | | | | |
|---|---|---|---|---|---|---|---|
|  | A | B | C | D | E | F | G |
| Coco glucoside [1] | 5 | 5 | 5 | 5 | 5 | 5 | 5 |
| Coco betaine [2] | 5.4 | 5.4 | 5.4 | 5.4 | 5.4 | 5.4 | 5.4 |
| Sodium lauryl ether carboxylate (5 EO) [3] | 3 | 3 | 3 | 3 | 3 | 3 | 3 |
| Sodium lauryl ether sulphate (2.2 EO) [4] | 4 | 4 | 4 | 4 | 4 | 4 | 4 |
| Poly(dimethyldiallyl-ammonium chloride) at 40% by weight in non-stabilized water [5] | 1 | — | — | 1 | — | — | — |
| Poly(vinylamine/N-vinylformamide) [6] | — | 1 | — | — | 1 | — | — |
| Polyurethane constituted of α,ω-dihydroxy polyolefin (KRASOL LBHP 2000)/ NMDEA/IPDI (67.9%/ 18.7%/23.4%) [7] | — | — | 1 | — | — | 1 | 1 |
| Benzophenone-4 | — | — | — | — | — | — | 5 |
| Zinc gluconate [8] | 6.5 | 6.5 | 6.5 | — | — | — | 6.5 |
| Zinc sulphate [9] | — | — | — | 4 | 4 | 4 | — |
| Preservative | qs | qs | qs | qs | qs | qs | qs |
| Fragrance | qs | qs | qs | qs | qs | qs | qs |
| Buffer | qs pH = 5 | qs pH = 5 | qs pH = 5 | qs pH = 5 | qs pH = 5 | qs pH = 5 | qs pH = 5 |
| Water | qs for 100 | qs for 100 | qs for 100 | qs for 100 | qs for 100 | qs for 100 | qs for 100 |
| Weight Ratio R [10] | 18.7 | 18.7 | 18.7 | 10.7 | 10.7 | 10.7 | 18.7 |

[1] PLANTACARE 818 UP sold by Cognis
[2] DEHYTON AB 30 sold by Cognis
[3] AKYPO RLM 45 CA sold by Kao
[4] TEXAPON N 702 sold by Cognis
[5] MERQUAT 100 sold by Nalco
[6] CATIOFAST VMP sold by BASF
[7] Polyurethane as described in French Patent Application No. FR 2 898 603; the percentage of each of the monomers is expressed by weight
[8] GIVOBIO G Zn sold by SEPPIC
[9] sold by SEPPIC
[10] R = (the amount of anionic, amphoteric and/or zwitterionic, and non-ionic surfactants)/(amount of zinc element of zinc salt)

Results:

These compositions applied as shampoos after oxidation dyeing gave a better color fastness than conventional shampoos containing the same amount of UV-screening agents.

What is claimed is:

1. A cosmetic composition for washing and/or cleansing keratin fibers, comprising:
    at least one anionic surfactant (A) comprising, in its structure, at least one group chosen from sulphate, sulphonate, and phosphate groups, chosen from alkyl sulphates, alkylamido sulphates, alkyl ether sulphates, alkylamido ether sulphates, alkylaryl ether sulphates, alkyl ether sulphosuccinates, acyl isethionates, methyl acyl taurates, and salts thereof, wherein the alkyl or acyl group of the at least one surfactant (A) comprises from 8 to 24 carbon atoms, and the aryl group of the at least one surfactant (A) is chosen from phenyl and benzyl groups,
    at least one carboxylic anionic surfactant (B) other than the at least one anionic surfactant (A) chosen from polyoxyalkylenated ($C_6$-$C_{24}$)alkyl ether carboxylic acids comprising from 2 to 50 ethylene oxide groups, polyoxyalkylenated ($C_6$-$C_{24}$)alkylaryl ether carboxylic acids comprising from 2 to 50 ethylene oxide groups, polyoxyalkylenated ($C_6$-$C_{24}$)alkylamido ether carboxylic acids comprising from 2 to 50 ethylene oxide groups, and salts thereof,
    at least one amphoteric or zwitterionic surfactant (C) chosen from aliphatic secondary amine derivatives and aliphatic tertiary amine derivatives, and further wherein at least one aliphatic substituent of the secondary amine derivatives and the tertiary amine derivatives is chosen from linear or branched chains comprising from 8 to 22 carbon atoms and at least one group chosen from water-soluble anionic groups and betaine groups,
    at least one alkyl(poly)glycoside non-ionic surfactant (D) chosen from compounds of formula (IV):

$$R_1O\text{---}(R_2O)_t(G)_v \quad (IV)$$

wherein:
    $R_1$ is chosen from linear and branched, saturated and unsaturated alkyl groups comprising from about 8 to 24 carbon atoms, and alkylphenyl groups comprising linear and branched alkyl group comprising from 8 to 24 carbon atoms;
    $R_2$ is chosen from alkylene groups comprising from about 2 to 4 carbon atoms;
    G is chosen from sugar units comprising from 5 to 6 carbon atoms;
    t is chosen from a number ranging from 0 to 10; and
    v is chosen from a number ranging from 1 to 15,
    at least one cationic polymer (E) chosen from alkyldiallylamine cyclopolymers and dialkyldiallylammonium cyclopolymers, which are homopolymers or copolymers comprising, as main constituents of the chain, units corresponding to formulae (IX) or (X):

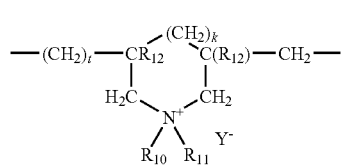

(IX)

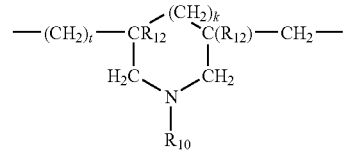

(X)

wherein:
k and t are equal to 0 or 1, the sum of k and t being equal to 1;
$R_{12}$ is chosen from hydrogen and methyl;
$R_{10}$ and $R_{11}$ are independently chosen from alkyl groups comprising from 1 to 6 carbon atoms, hydroxyalkyl groups comprising a $C_1$-$C_5$ alkyl group, and lower amidoalkyl groups comprising a $C_1$-$C_4$ alkyl group, or
$R_{10}$ and $R_{11}$ form, together with the nitrogen atom to which they are attached, a heterocyclic group;
$Y^-$ is an anion chosen from bromide, chloride, acetate, borate, citrate, tartrate, bisulphate, bisulphite, sulphate, and phosphate,
at least one water-soluble zinc salt (F) chosen from zinc sulphate, zinc chloride, zinc lactate, zinc gluconate, zinc phenolsulphonate, zinc salicylate, and derivatives thereof, and
optionally at least one UV-screening agent (G),
wherein the weight ratio of the total amount of the surfactants (A), (B), (C), and (D) to the amount of zinc element of the at least one zinc salt has a value ranging from 10 to 25;
wherein the at least one surfactant (A) is present in an amount ranging from 2% to 25% by weight, relative to the total weight of the cosmetic composition;
wherein the at least one surfactant (B) is present in an amount ranging from 1% to 10% by weight, relative to the total weight of the cosmetic composition;
wherein the at least one surfactant (C) is present in an amount ranging from 1% to 15% by weight, relative to the total weight of the cosmetic composition;
wherein the at least one surfactant (D) is present in an amount ranging from 1% to 15% by weight, relative to the total weight of the cosmetic composition; and
wherein the at least one cationic polymer (E) is present in an amount ranging from 0.1% to 5% by weight, relative to the total weight of the cosmetic composition.

2. The cosmetic composition according to claim 1, wherein the total amount of the at least one anionic surfactant (A), the at least one carboxylic anionic surfactants (B), the at least one surfactant (C), and the at least one alkyl(poly)glycoside non-ionic surfactant (D) ranges from 6% to 35% by weight, relative to the total weight of the cosmetic composition.

3. The cosmetic composition according to claim 1, wherein at least one weight ratio chosen from the weight ratios of:
    the amount of the at least one surfactant (A) to the amount of the at least one surfactant (B),
    the amount of the at least one surfactant (A) to the amount of the at least one surfactant (C),
    the amount of the at least one surfactant (A) to the amount of the at least one surfactant (D), and
    the amount of the at least one surfactant (B) to the amount of the at least one surfactant (C), has a value ranging from 0.1 to 10.

4. The cosmetic composition according to claim 3, wherein all of the weight ratios of:
the amount of the at least one surfactant (A) to the amount of the at least one surfactant (B),
the amount of the at least one surfactant (A) to the amount of the at least one surfactant (C),
the amount of the at least one surfactant (A) to the amount of the at least one surfactant (D), and
the amount of the at least one surfactant (B) to the amount of the at least one surfactant (C)
have a value ranging from 0.1 to 10.

5. The cosmetic composition according to claim 1, wherein the weight ratio of the amount of the at least one surfactant (B) to the amount of the at least one surfactant (C) has a value ranging from 0.1 to 10.

6. The cosmetic composition according to claim 5, wherein the weight ratio of the amount of the at least one surfactant (B) to the amount of the at least one surfactant (C) has a value ranging from 0.3 to 2.

7. The cosmetic composition according to claim 1, wherein the salt of the at least one surfactant (A) is chosen from alkali metal salts; ammonium salts; amine salts, and magnesium salts of said surfactants chosen from alkyl sulphates, alkylamido sulphates, alkyl ether sulphates, alkylamido ether sulphates, alkylaryl ether sulphates, alkyl ether sulphosuccinates, acyl isethionates, and methyl acyl taurates.

8. The cosmetic composition according to claim 7, wherein said the at least one amine salt is chosen from amino alcohol salts.

9. The cosmetic composition according to claim 1, wherein the at least one surfactant (A) is oxyethylenated and/or oxypropylenated.

10. The cosmetic composition according to claim 1, wherein the water-soluble anionic groups are chosen from carboxylate, sulphonate, sulphate, phosphate, and phosphonate group; and wherein the betaines groups are chosen from $(C_8-C_{20})$alkylbetaines, sulphobetaines, $(C_8-C_{20})$alkylamido$(C_1-C_6)$alkylbetaines, and $(C_8-C_{20})$alkylamido$(C_1-C_6)$alkylsulphobetaines, and the betaines groups are optionally hydroxylated.

11. The cosmetic composition according to claim 1, wherein the at least one zinc salt (F) is chosen from zinc sulphate, zinc chloride, and zinc gluconate.

12. The cosmetic composition according to claim 1, wherein the zinc element of the at least one zinc salt (F) is present in an amount of less than 2% by weight, relative to the total weight of the cosmetic composition.

13. The cosmetic composition according to claim 12, wherein the zinc element of the at least one zinc salt (F) is present in an amount ranging from 0.005% to 1.5% by weight, relative to the total weight of the cosmetic composition.

14. The cosmetic composition according to claim 1, wherein the at least one UV-screening agent (G) optionally present is chosen from:
dibenzoylmethane derivatives;
anthranilates;
cinnamic derivatives;
salicylic derivatives;
camphor derivatives;
benzophenone derivatives;
β, β-diphenylacrylate derivatives;
triazine derivatives;
benzotriazole derivatives;
benzalmalonate derivatives;
benzimidazole derivatives;
imidazolines;
bisbenzoazolyl derivatives;
p-aminobenzoic acid (PABA) derivatives;
benzoxazole derivatives;
screening polymers and screening silicones;
dimers derived from a-alkylstyrene; and
4,4-diarylbutadienes.

15. The cosmetic composition according to claim 1, wherein the at least one UV-screening agent is present in an amount ranging from 0.01% to 20% by weight, relative to the total weight of the cosmetic composition.

16. A process for washing and/or cleansing keratin fibers, comprising applying to the keratin fibers a cosmetic composition according to claim 1; and
optionally kneading the hair, and rinsing the hair.

17. A process for protecting the color of keratin fibers from sunlight and/or repeated washing, comprising applying to the keratin fibers a cosmetic composition according to claim 1; and
optionally kneading the hair, and rinsing the hair.

18. A multi-compartment kit for dyeing keratin fibers, comprising:
at least one compartment comprising at least one dyeing composition chosen from one-part and two-part oxidation dye and direct dye compositions; and
at least one compartment comprising a cosmetic composition according to claim 1.

* * * * *